(12) United States Patent
Hannibal et al.

(10) Patent No.: US 12,115,389 B2
(45) Date of Patent: *Oct. 15, 2024

(54) MOTION ENABLE MECHANISM WITH CAPACITIVE SENSOR

(71) Applicant: Varian Medical Systems, Inc., Palo Alto, CA (US)

(72) Inventors: Ross Hannibal, Saratoga, CA (US); Wade Curtiss, Sunnyvale, CA (US)

(73) Assignee: VARIAN MEDICAL SYSTEMS, INC., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/227,992

(22) Filed: Jul. 31, 2023

(65) Prior Publication Data

US 2023/0372737 A1 Nov. 23, 2023

Related U.S. Application Data

(63) Continuation of application No. 17/685,411, filed on Mar. 3, 2022, now Pat. No. 11,745,030, which is a
(Continued)

(51) Int. Cl.
*A61N 5/10* (2006.01)
*A61B 6/46* (2024.01)
(Continued)

(52) U.S. Cl.
CPC ............ *A61N 5/1048* (2013.01); *A61B 6/461* (2013.01); *A61B 6/467* (2013.01); *H01H 9/161* (2013.01);
(Continued)

(58) Field of Classification Search
CPC ....... H03K 17/955; H03K 2217/94036; H03K 2217/94052
See application file for complete search history.

(56) References Cited

U.S. PATENT DOCUMENTS 4,987,583 A * 1/1991 Travanty ................ A61B 6/102
378/197
5,212,621 A 5/1993 Panter
(Continued)

OTHER PUBLICATIONS

Thomas Maier et al., "Joystick Control with Capacitive Release Switch for a Microsurgical Telemanipulator", In: Proc 2919 IEEE Human System Interaction, 2010, pp. 223-229.

*Primary Examiner* — Rexford N Barnie
*Assistant Examiner* — David A Shiao
(74) *Attorney, Agent, or Firm* — SU IP CONSULTING (57) ABSTRACT

A motion-enable device includes a mechanical switch and a capacitive sensor with a sensing region that is located adjacent to the mechanical switch. The mechanical switch enables a first signal when closed or actuated that indicates that the mechanical switch is in an active state. The capacitive sensor enables a second signal when a conductive object is disposed in the sensing region, where the second signal indicates that the capacitive sensor is in an active state. Enablement of operation of an apparatus depends on receipt of both the first signal and the second signal. The mechanical switch and the capacitive sensor act as the two separate switches required by functional safety requirements for a motion enable device. Because the sensing region of the capacitive sensor is adjacent to the mechanical switch, the first and second signals are generated when an operator actuates the mechanical switch with a single digit.

16 Claims, 8 Drawing Sheets

Related U.S. Application Data continuation of application No. 15/957,727, filed on Apr. 19, 2018, now Pat. No. 11,278,739.

(60) Provisional application No. 62/566,301, filed on Sep. 29, 2017.

(51) Int. Cl.

| | | |
|---|---|---|
| *H01H 9/16* | (2006.01) | |
| *H01H 13/02* | (2006.01) | |
| *H01H 13/70* | (2006.01) | |
| *H05G 1/56* | (2006.01) | |
| *H05G 1/58* | (2006.01) | |
| *A61B 6/04* | (2006.01) | |
| *A61B 17/00* | (2006.01) | |
| *H03K 17/18* | (2006.01) | |
| *H03K 17/955* | (2006.01) | |
| *H03K 17/96* | (2006.01) | |

(52) U.S. Cl.
CPC .......... *H01H 13/023* (2013.01); *H01H 13/70* (2013.01); *H05G 1/56* (2013.01); *H05G 1/58* (2013.01); *A61B 6/0487* (2020.08); *A61B 2017/00017* (2013.01); *A61B 2017/00199* (2013.01); *A61N 2005/1074* (2013.01); *H01H 2013/026* (2013.01); *H01H 2239/006* (2013.01); *H01H 2239/064* (2013.01); *H01H 2300/014* (2013.01); *H01H 2300/038* (2013.01); *H01H 2300/04* (2013.01); *H03K 17/18* (2013.01); *H03K 17/955* (2013.01); *H03K 17/96* (2013.01); *H03K 17/962* (2013.01)

(56) References Cited

U.S. PATENT DOCUMENTS

| | | |
|---|---|---|
| 5,341,036 A | 8/1994 | Wheeler et al. |
| 5,367,199 A | 11/1994 | Lefkowitz et al. |
| 8,669,949 B2 | 3/2014 | Cipriano et al. |
| 8,686,957 B2 | 4/2014 | Rip et al. |
| 8,692,815 B2 | 4/2014 | Deslippe et al. |
| 10,976,387 B1 | 4/2021 | Damadian et al. |
| 11,247,072 B2 | 2/2022 | Filiberti |
| 2001/0026266 A1 | 10/2001 | Schena et al. |
| 2002/0140440 A1* | 10/2002 | Haase .................. H03K 17/955 324/678 |
| 2004/0119484 A1* | 6/2004 | Basir ........................ G05G 5/28 324/680 |
| 2005/0179448 A1 | 8/2005 | Kirchner et al. |
| 2008/0130835 A1* | 6/2008 | Peterson ............... A61B 6/4464 378/117 |
| 2011/0113371 A1 | 5/2011 | Parker et al. |
| 2012/0043976 A1* | 2/2012 | Bokma ................. H03K 17/955 324/679 |
| 2012/0314841 A1 | 12/2012 | Heid |
| 2013/0077765 A1 | 3/2013 | Welsh |
| 2013/0221243 A1 | 8/2013 | Perkins |
| 2014/0267157 A1* | 9/2014 | Dorfner .................... G01D 5/24 345/174 |
| 2015/0203056 A1 | 7/2015 | Adkins et al. |
| 2015/0367776 A1 | 12/2015 | Salter et al. |
| 2016/0135779 A1 | 5/2016 | Kim et al. |
| 2017/0206720 A1 | 7/2017 | Ellis |
| 2017/0227118 A1 | 8/2017 | Buttolo et al. |
| 2018/0069549 A1* | 3/2018 | Cooper .................. H04M 1/026 |
| 2018/0292938 A1 | 10/2018 | Karlo et al. |
| 2019/0103869 A1 | 4/2019 | Hannibal et al. |
| 2019/0252814 A1 | 8/2019 | Richardson et al. |
| 2022/0184420 A1 | 6/2022 | Hannibal et al. |

* cited by examiner

MOTION ENABLE MECHANISM WITH CAPACITIVE SENSOR

CROSS-REFERENCE TO RELATED APPLICATIONS

The present application is a continuation under 35 U.S.C. § 120 of U.S. patent application Ser. No. 17/685,411, filed Mar. 3, 2022, which is a continuation of U.S. application Ser. No. 15/957,727, filed Apr. 19, 2018, and now U.S. Pat. No. 11,278,739, which claims the benefit of U.S. Provisional Application No. 62/566,301, filed Sep. 29, 2017. The aforementioned U.S. Patent Applications and U.S. Provisional Application, including any appendices or attachments thereof, are hereby incorporated by reference in their entirety.

BACKGROUND

Unless otherwise indicated herein, the approaches described in this section are not prior art to the claims in this application and are not admitted to be prior art by inclusion in this section.

The motion enable switch (also referred to as a "dead man's switch) is a form of fail-safe device designed to stop the motion or operation of a machine in the absence of an active input from an operator. Motion enable switches are typically employed in situations in which unwanted motion of a mechanism can present a crush hazard or other dangerous situation to the operator or nearby persons. For example, in radiation therapy and medical imaging applications, a patient is precisely positioned for treatment or imaging via a movable couch, and a motion enable switch must be continuously depressed by the operator for couch motion to take place. Thus, couch motion only occurs while being observed and actively enabled by the operator, which greatly reduces the risk of patient collisions.

An additional functional safety requirement associated with some motion enable devices is the inclusion of two separate switches in the motion enable device, where motion is only enabled by the device when both switches are actively actuated by an operator. In radiation therapy and medical imaging applications, two adjacent mechanical buttons are often employed as the two separate switches of the motion enable device, and the operator depresses both buttons to cause the couch motion that positions a patient for treatment. One drawback to this approach is that, when positioning a patient, an operator is required to cock the wrist at an awkward angle while exerting significant pressure on the buttons. This is particularly true when the control interface is configured as a side panel or other vertical surface. Because this physically awkward operation may be performed dozens or hundreds of times per day, the operator can be susceptible to one or more repetitive stress injuries, such as carpal tunnel syndrome. Another drawback of the two mechanical button approach for motion enable of an apparatus is that if one of the two mechanical buttons has failed in the closed position, the potentially hazardous motion of the apparatus will be unexpectedly enabled when the single functioning button is depressed, which violates the functional safety standards developed by the International Electrotechnical Commission (IEC). Further, detection of such a failure can be problematic, since motion of the device will appear to be enabled normally, by depressing two mechanical buttons, until unexpected motion occurs when only the single functioning button is depressed.

In light of the above, there is a need in the art for a motion enable system that addresses the above-described challenges.

BRIEF DESCRIPTION OF THE DRAWINGS

Features of the present disclosure will become more fully apparent from the following description and appended claims, taken in conjunction with the accompanying drawings. These drawings depict only several embodiments in accordance with the disclosure and are, therefore, not to be considered limiting of its scope. The disclosure will be described with additional specificity and detail through use of the accompanying drawings.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the disclosure, as generally described herein, and illustrated in the figures, can be arranged, substituted, combined, and designed in a wide variety of different configurations, all of which are explicitly contemplated and make part of this disclosure.

As noted above, the use of two adjacent mechanical buttons in a motion enable device can result in repetitive stress injuries in an operator. According to various embodiments, a motion-enable device includes a mechanical switch, such as a button mechanism, and a capacitive sensor with a sensing region that is located adjacent to the mechanical switch. The mechanical switch is configured to enable a first signal when closed or actuated, where the first signal indicates that the mechanical switch is in an active state. The capacitive sensor is configured to enable a second signal when a conductive object (such as a digit of an operator) is disposed in the sensing region, where the second signal indicates that the capacitive sensor is in an active state. Enablement of operation or motion of an apparatus depends on receipt of both the first signal and the second signal. As a result, the mechanical switch and the capacitive sensor effectively act as the two separate switches required by the IEC functional safety requirements for a motion enable device. Because the sensing region of the capacitive sensor is adjacent to the mechanical switch, the first and second signals are generated when an operator actuates the mechanical switch with a single digit or conductive object. Thus, operation or motion of the apparatus is enabled when an operator actuates the mechanical switch with a single digit.

Figure 1:
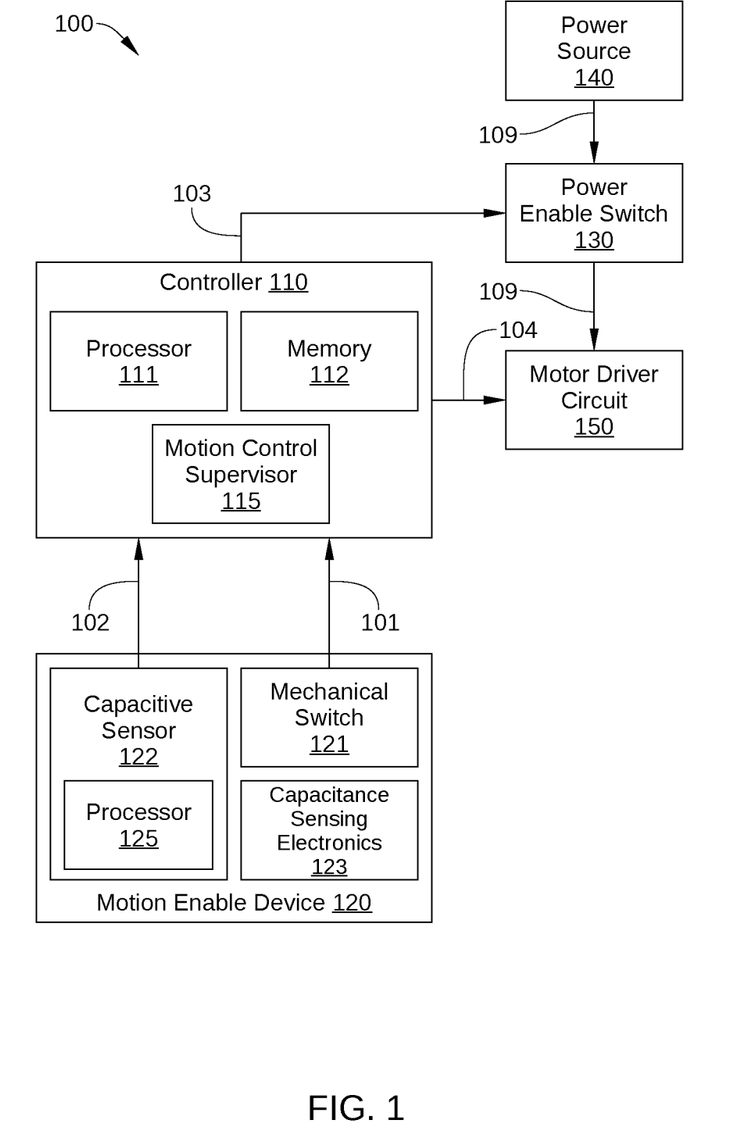
FIG. 1 schematically illustrates a motion enable system, according to various embodiments of the present disclosure.

FIG. 1 schematically illustrates a motion enable system 100, according to various embodiments of the present disclosure. Motion enable system 100 includes a controller 110, a motion enable device 120, and a power enable switch 130, and is configured to prevent unintended operation of or motion associated with a particular apparatus. In the embodiment illustrated in FIG. 1, the particular apparatus includes a motor driver circuit 150. In addition, motion enable system 100 is configured to enable operation of or motion associated with motor driver circuit 150 when an operator actively actuates a mechanical switch included in motion enable device 120. In other embodiments, motor driver circuit 150 can be any technically feasible actuator that can be controlled by controller 110 to produce an output motion.

Controller 110 controls the operation of motion enable system 100, including receiving a mechanical switch active signal 101 and a capacitive sensor active signal 102 from motion enable device 120 and, when certain conditions are met, transmitting a power enable signal 103 to power enable switch 130. For example, in some embodiments, controller 110 transmits power enable signal 103 to power enable switch 130 when a capacitive sensor of motion enable device 120 is active, as described below. In addition, controller 110 transmits one or more control signals 104 to motor driver circuit 150 that include motion inputs for a targeted motion of the apparatus associated with motor driver circuit 150, typically in response to a physical input from an operator via motion enable device 120. For example, in some embodiments, controller 110 transmits one or more control signals 104 to motor driver circuit 150 when an operator depresses or otherwise actuates a mechanical switch 121 included in motion enable device, as described below. Generally, controller 110 transmits the one or more control signals 104 to motor driver circuit 150 when certain conditions are met, such as the receipt of mechanical switch active signal 101 and a capacitive sensor active signal 102. In some embodiments, controller 110 includes a processor 111 and a memory 112.

Processor 111 is communicatively coupled to memory 112 and/or a non-volatile data storage medium such as a solid-state drive (SSD). Processor 111 may be any suitable processor implemented as a CPU, an application-specific integrated circuit (ASIC), a field programmable gate array (FPGA), any other type of processing unit, or a combination of different processing units. In general, processor 111 may be any technically feasible hardware unit capable of processing data and/or executing software applications residing in memory 112 or in firmware (not shown). Processor 111 is configured to read data from and write data to memory 112 and/or firmware. Memory 112 may include a random access memory (RAM) module, a flash memory unit, any other type of memory unit, or a combination thereof. Memory 112 may be used for data storage, and may include various software programs that can be executed by processor 111 and application data associated with said software programs. For example, in some embodiments, controller 110 includes a motion control supervisor 115 that can be implemented as a software program executed by processor 111 and/or as firmware (not shown) included in controller 110. In such embodiments, motion control supervisor 115 is responsible for generating appropriate control signals 104 to cause a targeted motion trajectory of a motor (not shown) or other actuator included in motor driver circuit 150. In the embodiment illustrated in FIG. 2, memory 112 is depicted as a separate device from processor 111, but in other embodiments memory 112 can be included in processor 111.

Power enable switch 130 is configured to selectively enable a power connection 109 from a power source 140 to motor driver circuit 150, in response to receiving power enable signal 103 from controller 110. In some embodiments, power enable switch 130 is an electronic circuit or firmware switch, rather than a mechanical switch. In such embodiments, power enable switch 130 can be implemented as part of controller 110 or as a separate entity.

Motor driver circuit 150 is configured to generate a physical output of an apparatus associated with motor driver circuit 150, such as a targeted motion of the apparatus. For example, in some embodiments, motor driver circuit 150 includes a motor for positioning a patient couch of a radiation therapy system along one axis of motion, for example a longitudinal axis, a lateral axis, or a vertical axis. As such, when power connection 109 to power source 140 is enabled and motor driver circuit 150 has received one or more control signals 104 from controller 110, control signals 104 cause the motor of motor driver circuit 150 to generate a suitable output motion. In some embodiments, control signals 104 can be any technically feasible control signal that can be used to control the output motion of motor driver circuit 150, including an analog signal, a digital signal, a serial signal, a pulse-width modulated signal, and the like.

Motion enable device 120 includes a mechanical switch 121 and a capacitive sensor 122. In some embodiments, motion enable device 120 is configured so that, when an operator provides an active input to mechanical switch 121, capacitive sensor 122 becomes active before mechanical switch 121 becomes active. Thus, in such embodiments, when the operator provides the active input to mechanical switch 121, capacitive sensor 122 generates, enables, and/or transmits capacitive switch active signal 102 before mechanical switch 121 generates, enables, and/or transmits mechanical switch active signal 101. Alternatively, in some embodiments, motion enable device 120 is configured so that, when an operator provides an active input to mechanical switch 121, capacitive sensor 122 becomes active at substantially the same time that mechanical switch 121 becomes active.

Mechanical switch 121 can be any technically feasible device or apparatus that, when actuated from a first position to a second position, enables mechanical switch active signal 101. For example, in some embodiments, mechanical switch 121 includes a button mechanism that remains in an open or inactive position except when actively depressed, for example by a spring-return mechanism or elastic member. In such embodiments, when the button mechanism of mechanical switch 121 is depressed and is in a closed or active position, an electrical connection is created that enables mechanical switch active signal 101 and/or causes transmission of mechanical switch active signal 101 to controller 110. Conversely, when the button mechanism of mechanical switch 121 stops being depressed by the operator, the spring-return mechanism or elastic member returns mechanical switch 121 to the open position. In another such embodiment, mechanical switch 121 includes a two-position toggle switch, or any other two-position switch mechanism that can be configured to remains in an open or inactive position except when actively depressed and returns to the open or inactive position when no longer depressed.

Capacitive sensor 122 can be any technically feasible capacitive sensor configured to enable capacitive sensor active signal 102 and/or transmit capacitive active sensor signal 102 to controller 110 when a user digit or other conductive object is detected in a sensing region (not shown in FIG. 1) of capacitive sensor 122. For example, in some embodiments, capacitive sensor 122 includes a projected capacitance device with a sensing region. In such embodiments, when a conductive object enters the sensing region, such as a digit of an operator or a conductive stylus, capacitive sensor 122 detects the presence of the conductive object before the conductive object contacts a surface of capacitive sensor 122. Capacitive sensor 122 can be configured for use with any suitable conductive object, including a single digit of an operator, an active conductive stylus, a passive conductive stylus, and the like. In some embodiments, capacitive sensor 122 is configured as a mutual capacitive sensor, and in other embodiments capacitive sensor 122 is configured as a self-capacitive sensor. Furthermore, capacitive sensor 122 can include any other technically feasible capacitive sensor that can detect the presence of a conductive member in the sensing region of capacitive sensor 122.

In some embodiments, capacitive sensor 122 includes various capacitance-sensing electronics 123, such as a single capacitive sensor element or an array of capacitive sensor elements that generate the electric field forming the sensing region of capacitive sensor 102. Capacitance-sensing electronics 123 may further include an excitation source couple to the capacitive sensor element(s) for refreshing the electric field, a capacitance-to-digital converter, and/or compensation circuitry for ensuring accurate capacitance detection in different conditions. In some embodiments, capacitance-sensing electronics further includes logic, such as firmware or locally-executed software that 1) determines whether a change in field strength measured by the capacitance-to-digital converter corresponds to a conductive object entering the sensing region of capacitive sensor 102, and 2) transmits capacitive sensor active signal 102 when appropriate. Alternatively, in some embodiments, such logic can reside in controller 110, and capacitive sensor active signal 102 then includes an analog or digital signal that is based on a change in field strength measured by the capacitance-to-digital converter.

In some embodiments, capacitive sensor 122 is configured with a sensing region that is adjacent to or extends past an interface surface of mechanical switch 121. Thus, in such embodiments, when an operator performs a physical input using mechanical switch 121 with a conductive object, the conductive object enters the sensing region of capacitive sensor 122 before reaching the interface surface of mechanical switch 121. As a result, motion enable device 120 is configured to generate or enable capacitive sensor active signal 102 prior to generating or enabling mechanical switch active signal 101. One such embodiment is illustrated in FIG. 2.

Figure 2:
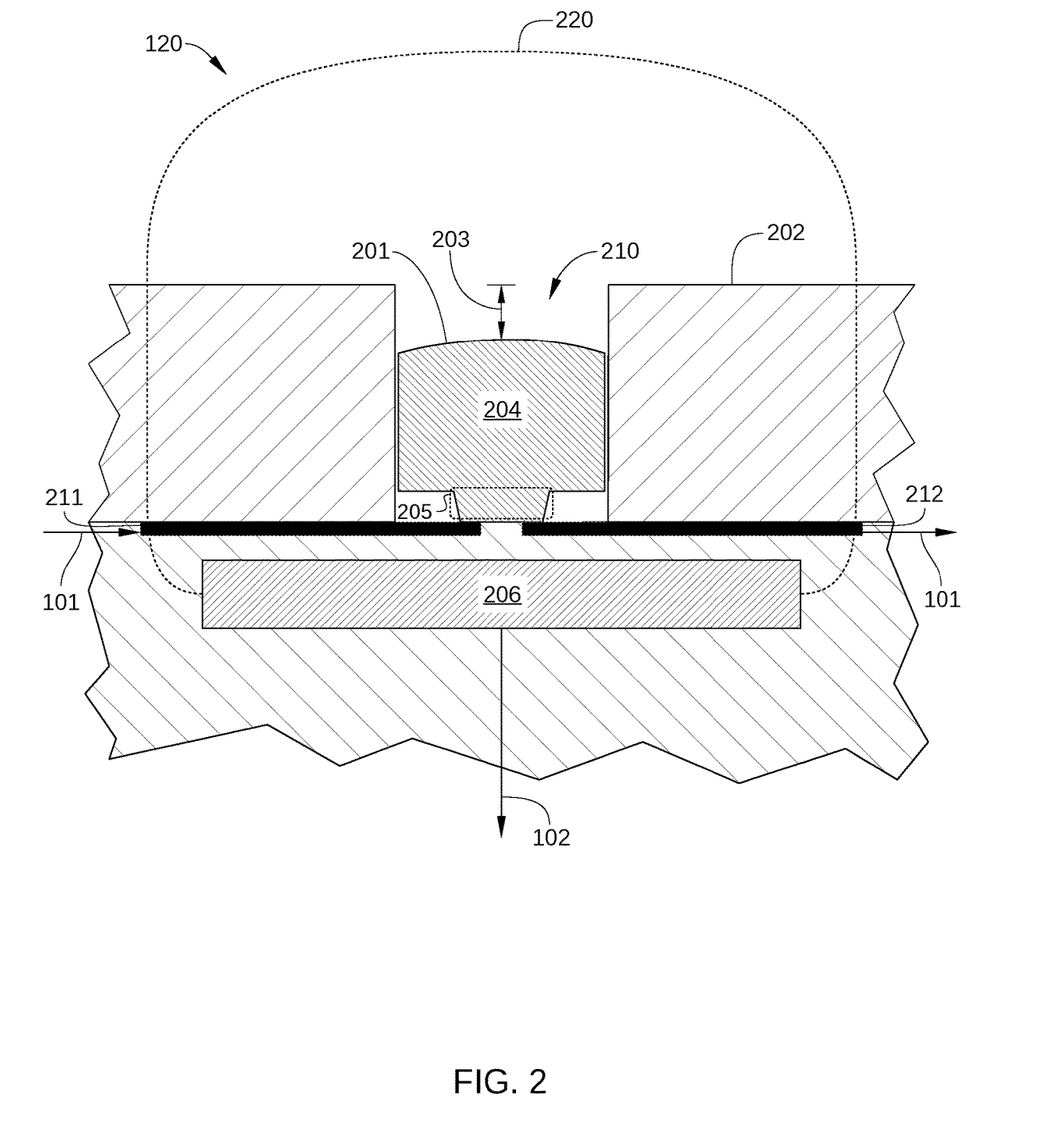
FIG. 2 is a schematic cross-sectional view of motion enable device, according to various embodiments of the present disclosure.

FIG. 2 is a schematic cross-sectional view of motion enable device 120, according to various embodiments of the present disclosure. Motion enable device 120 includes a button 210 with an interface surface 201 that is recessed from a surrounding surface 202 of motion enable device 120 by a recess distance 203. Recess distance 203 prevents accidental contact with motion enable device 120 from causing button 210 to be depressed, such via unintended contact with an elbow or shoulder. Recess distance 203 can be any suitable distance that reduces the likelihood of unintended contact with interface surface 201. Thus, for buttons 210 that are relatively large, recess distance 203 can be greater than for button 210 that are relatively small.

Motion enable device 120 is configured to enable mechanical switch active signal 101 when actuated (or depressed) from an open position to a closed position. In the embodiment illustrated in FIG. 2, motion enable device 120 enables mechanical switch active signal 101 by closing an electrical circuit between a first conductive contact or trace 211 and a second conductive contact or trace 212 when button 210 is depressed. Motion enable device 120 can be configured with any technically feasible button mechanism that closes the electrical circuit between first conductive contact or trace 211 and second conductive contact or trace 212. In some embodiments, button 210 includes a bulk region 204 that is at least partially formed from an elastic material, such as silicone rubber, and a compressible projection 205 that includes a material that increases in electrical conductivity when compressed, such as silicone rubber with conductive carbon particles suspended therein. In such embodiments, when button 210 is depressed by a conductive member, compressible projection 205 is compressed, the conductive particles suspended within compressible projection 205 come into contact with each other, and the flow of electricity between first conductive contact or trace 211 and second conductive contact or trace 212 is enabled.

Motion enable device 120 is further configured to enable capacitive sensor active signal 102 when a conductive member is disposed within a capacitive sensing region 220. To that end, motion enable device 120 includes a capacitive sensor 206 configured to generate capacitive sensing region 220. In embodiments in which capacitive sensing region 220 extends beyond interface surface 201 of button 210, motion enable device 120 enables capacitive sensor active signal 102 when a conductive object enters capacitive sensing region 220 and before button 210 is depressed or actuated into the active position. Thus, in such embodiments, when an operator initiates an input via motion enable device 120, motion enable device 120 is configured to enable capacitive sensor active signal 102 before enabling mechanical switch active signal 101. In some embodiments, capacitive sensing region 220 extends past the interface surface by at least about 2 mm, but no more than about 20 mm, to prevent unintended enablement or transmission of capacitive sensor active signal 101 when an operator is proximate motion enable device 120 but is not performing a physical input to motion enable device 120.

Figure 3:
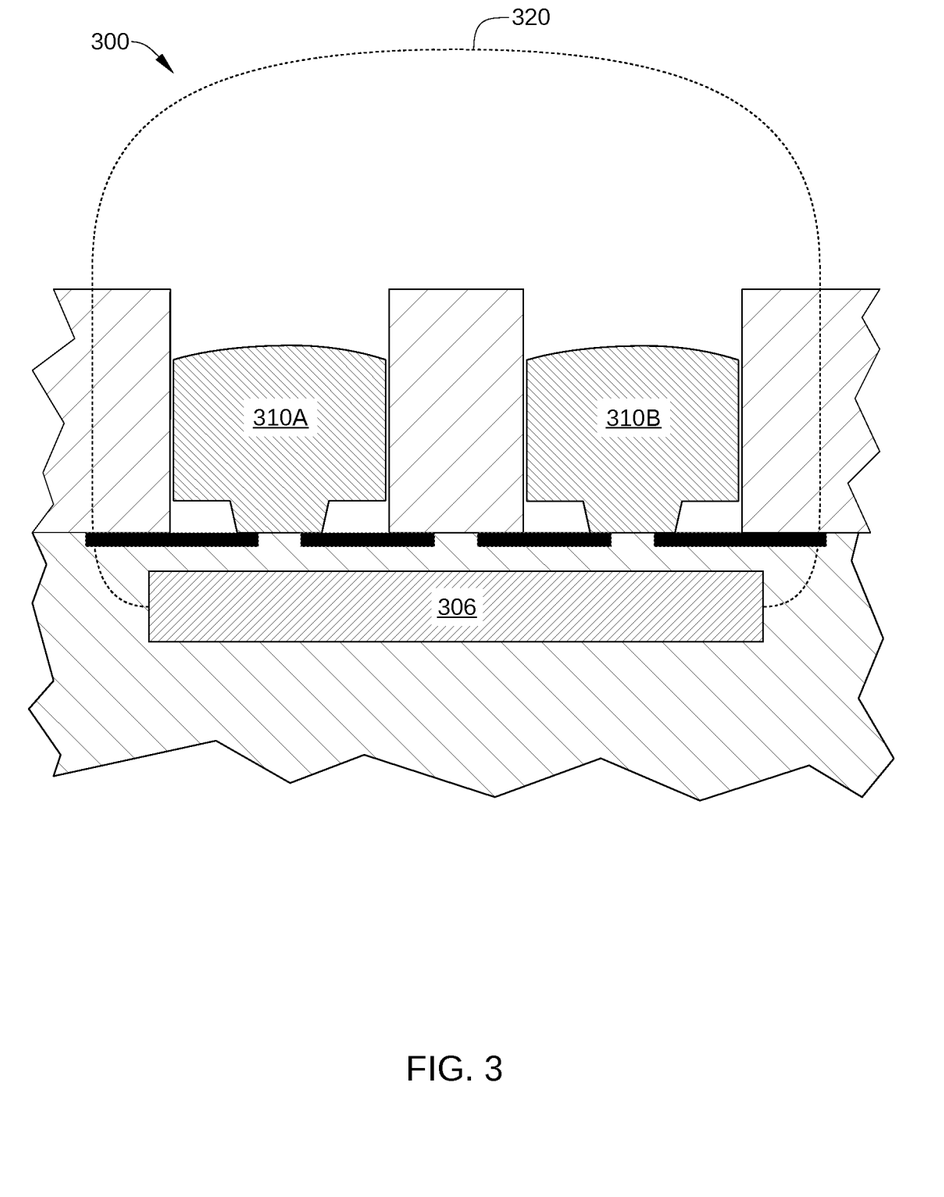
FIG. 3 is a schematic cross-sectional view of a motion enable device, according to various embodiments of the present disclosure.

In some embodiments, a capacitive sensor included in a motion enable device is associated with multiple mechanical switches. One such embodiment is illustrated in FIG. 3. FIG. 3 is a schematic cross-sectional view of a motion enable device 300, according to various embodiments of the present disclosure. Motion enable device 300 is substantially similar in configuration to motion enable device 120 in FIG. 2, except that motion enable device 300 includes a single capacitive sensor 306 that is associated with multiple buttons 310A and 310B. As shown, capacitive sensor 306 is configured to generate a capacitive sensing region 320 that extends beyond an interface surface 301A of button 310A and interface surface 301B of button 310B.

In some embodiments, buttons 310A and 310B make up a pair of input control buttons associated with a particular axis of motion of an apparatus. For example, in an embodiment in which buttons 310A and 310B are associated with a vertical axis of motion of a patient couch in a radiation therapy system, button 310A controls motion of the patient couch in the upward direction and button 310B controls motion of the patient couch in the downward direction. Thus, when an operator moves a digit or other conductive object within capacitive sensing region 320, power connection 109 is enabled via a power enable switch (such as power enable switch 130) between a power source (such as power source 140) and a motor driver circuit associated with moving the patient couch along the vertical axis of motion (such as motor driver circuit 150 in FIG. 1). One such embodiment is illustrated in FIG. 4.

Figure 4:
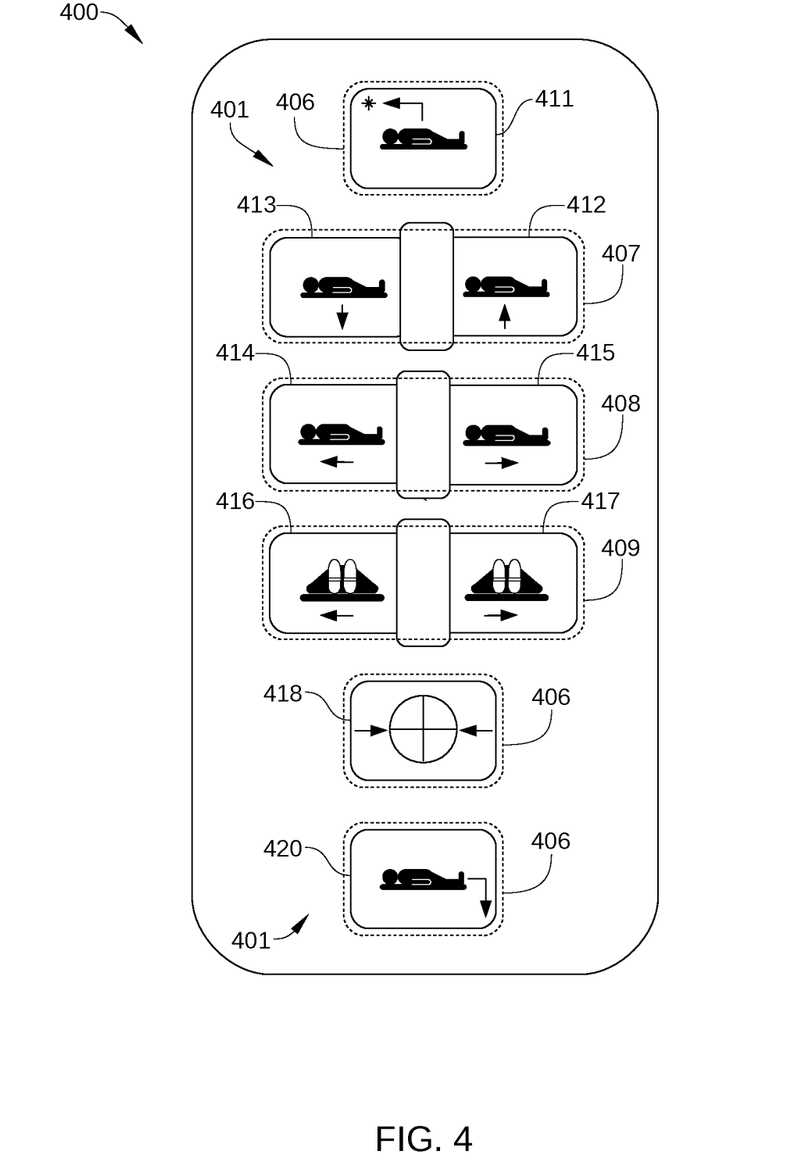
FIG. 4 schematically illustrates a user interface panel that includes a plurality of motion enable devices, according to an embodiment of the present disclosure.

FIG. 4 schematically illustrates a user interface panel 400 that includes a plurality of motion enable devices, according to an embodiment of the present disclosure. User interface panel 400 includes multiple mechanical buttons 401 that each control motion of a patient couch or other apparatus along one or more axes of motion. For example, the one or more axes of motion can include a vertical, a lateral, and a longitudinal axis of motion. In one such embodiment, a portion of buttons 401 are configured to initiate preprogrammed motion of a patient couch for a radiation therapy (RT) system along one or more of these axes, while other buttons 401 enable manual or preprogrammed control of the patient couch along a single axis of motion. In the embodiment illustrated in FIG. 4, user interface panel 400 includes an alignment button 411 that moves the patient couch to a virtual iso-center of the associated RT system, a vertical up button 412 for raising the patient couch, a vertical down button 413 for lowering the patient couch, a longitudinal in button 414 for moving the patient couch into the bore of the RT system, a longitudinal out button 415 for moving the patient couch out of the bore of the RT system, a lateral left button 416 for moving the patient couch to the left relative to the bore, a lateral right button 417 for moving the patient couch to the right relative to the bore, a load button 418 for moving the patient couch to the geometric iso-center of the RT system, and a home button 419 for unloading a patient, i.e., for moving the patient couch to a home position of the RT system. In some embodiments, user interface panel 400 includes more mechanical buttons 401 or fewer mechanical buttons 401 than those shown in FIG. 4.

Each of mechanical buttons 401 is associated with a capacitive sensor, and together with the associated capacitive sensor forms a motion enable device substantially similar to motion enable device 120, described above. Some of mechanical buttons 401 are associated with a single capacitive sensor. For example, in the embodiment illustrated in FIG. 4, alignment button 411, load button 418, and home button 419 are each associated with a single capacitive sensor 406. Alternatively or additionally, certain pairs of mechanical buttons 401 are associated with a single capacitive sensor. For example, in the embodiment illustrated in FIG. 4, vertical up button 412 and vertical down button 413 are both associated with a single capacitive sensor 407, longitudinal in button 414 and longitudinal out button 415 are both associated with a single capacitive sensor 408, and lateral left button 416 and lateral right button 417 are both associated with a single capacitive sensor 409.

In some embodiments, some of mechanical buttons 401 are configured as manual motion buttons that initiate motion of the patient couch in a particular direction. For example, in the embodiment illustrated in FIG. 4, manual motion buttons include vertical up button 412, vertical down button 413, longitudinal in button 414, longitudinal out button 415, lateral left button 416, and lateral right button 417. In some embodiments, some of mechanical buttons 401 are configured to initiate specific preprogrammed motions along one or more axes of motion. For example, in the embodiment illustrated in FIG. 4, preprogrammed motion buttons include alignment button 411, load button 418, and home button 419. It is noted that both manual motion buttons and preprogrammed motion buttons are generally configured to be part of a motion enable device similar to motion enable device 120 of FIG. 1.

User interface panel 400 enables an operator to perform manual inputs to initiate manual positioning and/or preprogrammed positioning of a patient couch (not shown), such as a patient couch of an RT system. User interface panel 400 may be located on a vertical surface 402 proximate the patient couch, for example on a stand and/or a vertical panel adjacent to the bore of the RT system. Alternatively, user interface panel 400 can be located on a hand-held control pendant that is communicatively connected with via a wired and/or wireless connection to a control system that receives inputs from the control pendant, such as controller 110.

When user interface panel 400 is so located, an operator can perform manual inputs into user interface panel 400 without bending or looking down. Further, for each motion enable device included in user interface panel 400, the operator can activate the two separate devices included therein with a single digit or conductive stylus. That is, the operator can activate both the mechanical switch and the capacitive sensor of a particular motion enable device by depressing the mechanical switch of that particular motion enable device with a single digit or conductive object, which is much more ergonomic than pressing two mechanical switches with two different digits, as illustrated in FIG. 5.

Figure 5:
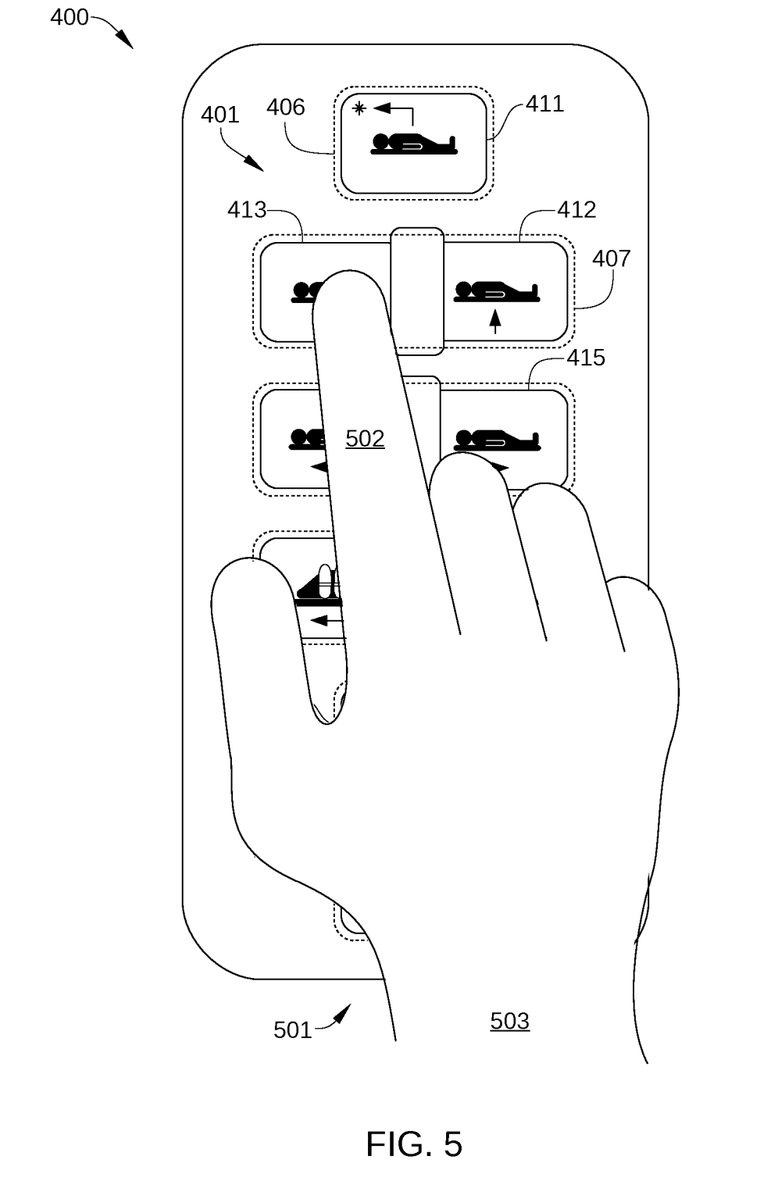
FIG. 5 schematically illustrates an operator hand depressing a vertical down button on a user interface panel, according to an embodiment of the present disclosure.

FIG. 5 schematically illustrates an operator hand 501 depressing vertical down button 413, according to an embodiment of the present disclosure. As shown, the operator can employ a single digit 502 to depress vertical down button 413 to enable motion of the patient couch vertically downward. As a result, the operator can keep wrist 503 straight while performing the targeted manual input into user interface panel 400. Therefore, as shown in FIG. 5, when continuously depressing any of mechanical buttons 401, such as vertical down button 413, the operator is at significantly reduced risk of repetitive stress injuries. Thus, the operator can perform manual inputs via user interface panel 400 safely and comfortably.

Figure 6:
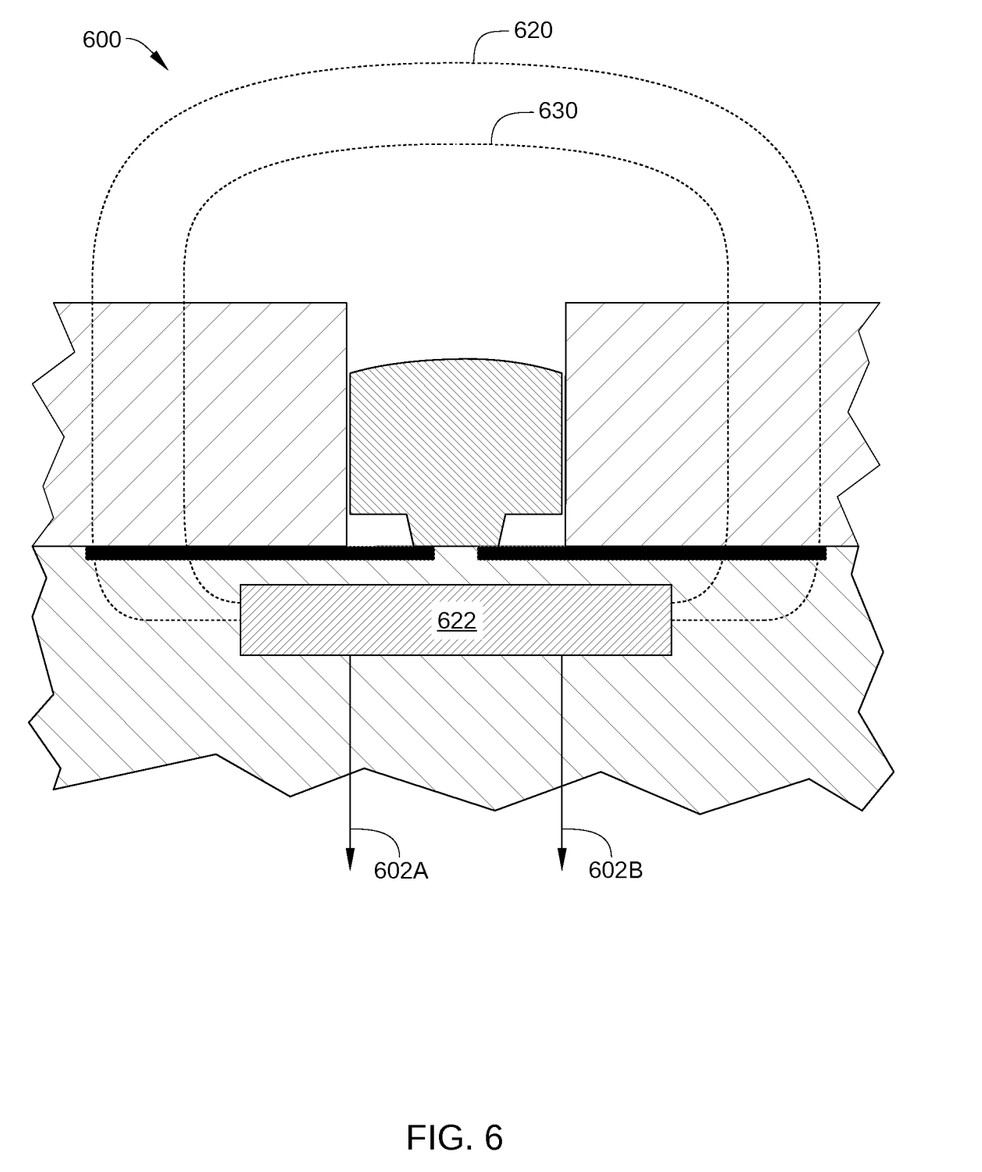
FIG. 6 is a schematic cross-sectional view of a motion enable device that generates an outer capacitive sensing region and an inner capacitive sensing region, according to various embodiments of the present disclosure.

In some embodiments, a capacitive sensor included in a motion enable device is configured with an outer capacitive sensing region and an inner capacitive sensing region, thereby enabling activation of the capacitive sensor when a conductive object enters a first smaller sensing region and deactivation of the capacitive sensor when the conductive object exits a second larger sensing region. One such embodiment is illustrated in FIG. 6. FIG. 6 is a schematic cross-sectional view of a motion enable device 600 that generates an outer capacitive sensing region 620 and an inner capacitive sensing region 630, according to various embodiments of the present disclosure. Motion enable device 600 is substantially similar in configuration to motion enable device 120 in FIG. 2, except that motion enable device 600 is configured with a capacitive sensor 622 that generates outer capacitive sensing region 620 and inner capacitive sensing region 630. In addition, motion enable device 600 is configured to transmit a first capacitive sensor active signal 602A when a user digit or other conductive object is detected in outer capacitive sensing region 620 and a second capacitive sensor active signal 602B when the user digit or other conductive object is detected in inner capacitive sensing region 630. In such embodiments, controller 110 can therefore determine whether a conductive object is within outer capacitive sensing region 620 or inner capacitive sensing region 630.

According to some embodiments, controller 110 changes capacitive sensor 622 from inactive to active when capacitive sensor 622 is currently inactive and a conductive object is detected within inner capacitive sensing region 630. By contrast, in such embodiments, controller 110 changes capacitive sensor 622 from active to inactive when capacitive sensor 622 is currently active and the conductive object is not detected within either inner capacitive sensing region 630 or outer capacitive sensing region 620. As a result, if an operator hovers a conductive object near motion enable switch 600, capacitive sensor 622 does not repeatedly change from active to inactive, as the conductive object enters and exits the capacitive sensing region. Instead, the operator would have to move the conductive object within inner capacitive sensing region 620, then out of outer capacitive sensing region 630 for controller 110 to change back to inactive. As a result, in such embodiments, transmission of power enable signal 103 to power enable switch 130 is not repeatedly initiated and then stopped when the operator hovers a conductive object near motion enable switch 600.

Figure 7:
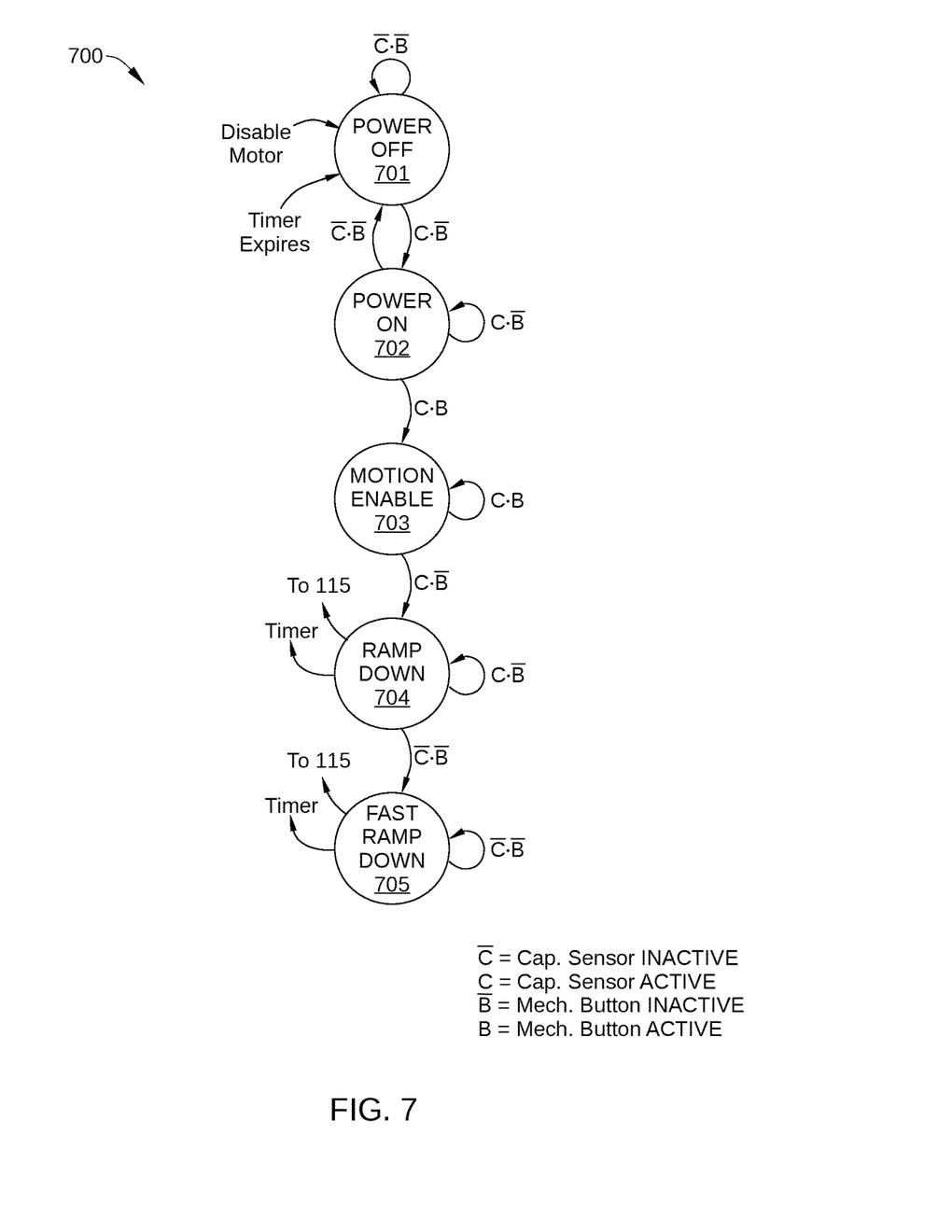
FIG. 7 illustrates a state diagram for the motion enable system in FIG. 1, according to various embodiments of the present disclosure.

FIG. 7 illustrates a state diagram 700 for motion enable system 100 in FIG. 1, according to various embodiments of the present disclosure. In the embodiment illustrated in FIG. 7, motion enable system 100 operates in five different power states: a Power Off state 701, a Power On state 702, a Motion Enable state 703, a Ramp Down state 704, and a Fast Ramp Down state 705. However, in other embodiments, motion enable system 100 can operate in additional states or in fewer states than those shown in FIG. 7.

In Power Off state 701, there is no power connection 109 between power source 140 and motor driver circuit 150, and the actuator associated with or included in motor driver circuit 150 cannot produce an output motion. Generally, when capacitive sensor 122 is inactive (no conductive object detected, denoted by C in FIG. 4) and mechanical switch 121 is inactive (not depressed/in open position, denoted by B in FIG. 4), motion enable system 100 is in Power Off state 701. In some embodiments, motion enable system 100 enters Power Off state 701 based on a decision by motion control supervisor 115, such as when a preprogrammed motion has been completed by an actuator associated with motor driver circuit 150. Alternatively or additionally, in some embodiments, motion enable system 100 enters Power Off state 701 when a fast ramp-down timer that is initiated in Ramp Down state 704 expires. The fast ramp-down timer is described below in conjunction with Ramp Down state 704.

In Power On state 702, power connection 109 is established between power source 140 and motor driver circuit 150. Generally, when controller 110 receives capacitive sensor active signal 102 from motion enable device 120 (i.e., a conductive object is detected and capacitive sensor 122 is active, denoted by C in FIG. 4), controller 110 transmits power enable signal 103 to power enable switch 130, and motion enable system 100 enters Power On state 702. In Power On state 702, the components of motor driver circuit 150 can begin powering up even though no control signals 104 have been received from controller 110. Thus, Power On state 702 allows motor drive circuit 150 to be prepared for operation before both switches of motion enable device 120 (i.e., mechanical switch 121 and capacitive sensor 122) have become active. As shown, in the embodiment illustrated in FIG. 7, when motion enable system 100 is in Power On state 702, controller 110 continuously confirms that mechanical switch 121 is inactive (i.e., mechanical switch active signal 101 has not been received from mechanical switch 121) and capacitive sensor 122 is active (i.e., capacitive sensor active signal 102 is being received from capacitive sensor 122).

In Motion Enable state 703, motor driver circuit 150 is powered and motion control supervisor 115 transmits any appropriate control signals 104 to motor driver circuit 150 to cause a targeted motion trajectory of a motor or other actuator included in motor driver circuit 150. In some embodiments, motion enable system 100 enters Motion Enable state 703 in response to controller 110 receiving or detecting mechanical switch active signal 101 and capacitive sensor active signal 102. That is, motion enable system 100 enters Motion Enable state 703 when a conductive object is detected (capacitive sensor 122 is active) and mechanical switch 121 is actuated and becomes active.

In some embodiments, upon entering Motion Enable state 703, motion control supervisor 115 determines whether there are any faults that prevent motion driver circuit from generating an output motion. If no faults are detected, motion control supervisor 115 then determines a target trajectory of the output motion of motor driver circuit 150, and transmits control signals 104 to motor driver circuit 150 suitable for causing the motor or actuator to generate the output motion that follows the targeted velocity profile.

In some embodiments, the target trajectory may include an S-curve acceleration profile for reducing or eliminating jerk. Alternatively or additionally, in some embodiments the target trajectory may include a constant output motion of motor driver circuit 150. In such embodiments, motion control supervisor 115 determines the target trajectory in response to an operator continuously depressing the mechanical switch 121 of motion enable device 120, or continuously performing any other suitable physical input with the mechanical switch 121. For example, when motor driver circuit 150 is associated with or includes a motor for positioning a patient couch longitudinally in an RT system, when an operator continuously depresses longitudinal in button 414 (shown in FIG. 4), motion control supervisor 115 transmits control signals 104 to motor driver circuit 150 that cause the motor to actuate the patient couch with a targeted velocity profile that includes an initial S-curve acceleration profile, then move at an initial longitudinal velocity. After the operator has depressed longitudinal in button 414 for longer that a specified time period (e.g., three seconds), motion control supervisor 115 then ramps the velocity to a higher longitudinal velocity.

In embodiments in which the operator provides a physical input to a motion enable device 120 that is associated with a preprogrammed motion, such as alignment button 411, load button 418, or home button 419 in FIG. 4, the target trajectory may further terminate with an S-curve deceleration profile for reducing or eliminating jerk. In such embodiments, motion control supervisor 115 generally stops sending any control signals 104 to motor driver circuit 150 once the preprogrammed motion is completed, even when controller 110 determines that capacitive sensor 122 and mechanical switch 121 are both active.

In Motion Enable state 703, when controller 110 determines that capacitive sensor 122 is active and mechanical switch 121 is not active, motion enable system 100 enters Ramp Down state 704. That is, when an operator stops depressing mechanical switch 121 with a conductive object (such as a digit or conductive stylus), but the conductive object is still within the capacitive sensing region of capacitive sensor 122, motion enable system 100 enters Ramp Down state 704.

In Ramp Down state 704, one of the two switches of motion enable device 120 is not active, and therefore motion of the motor or other actuator associated with motor driver circuit 150 should stop. In some embodiments, when motion enable system 100 enters Ramp Down state 704, motion control supervisor 115 determines a target trajectory for the motor or other actuator associated with motor driver circuit 150, and transmits control signals 104 to motor driver circuit 150 suitable for causing the motor or actuator to generate the output motion that follows the targeted velocity profile. In some embodiments the target trajectory may include an S-curve deceleration profile that minimizes or eliminates jerk. Thus, in Ramp Down state 704, when an operator stops depressing or actuating mechanical switch 121 of motion enable device 120, controller 110 stops the output motion of motor driver circuit 150 according to a smooth deceleration curve.

In some embodiments, while motion enable system 100 is in Ramp Down state 704, controller 110 initiates a fast ramp-down timer. Upon expiration of the fast ramp-down timer, controller 110 stops sending power enable signal 103 to power enable switch 130, and motor control circuit 150 is not longer powered. In some embodiments, the fast ramp-down timer is on the order of about 500 ms to about two seconds.

In Ramp Down state 704, when controller 110 determines that capacitive sensor 122 is not active and mechanical switch 121 is also not active, motion enable system 100 enters Fast Ramp Down state 705. That is, when an operator stops depressing mechanical switch 121 with a conductive object (such as a digit or conductive stylus) and the conductive object is also no longer within the capacitive sensing region of capacitive sensor 122, motion enable system 100 enters Fast Ramp Down state 705.

In Fast Ramp Down state 705, the two switches of motion enable device 120 are both inactive, and therefore motion of the motor or other actuator associated with motor driver circuit 150 should stop within a distance that satisfies an IEC stopping distance for the actuator or motor associated with motor driver circuit 150. In some embodiments, when motion enable system 100 enters Fast Ramp Down state 705, motion control supervisor 115 determines a target trajectory for the motor or other actuator associated with motor driver circuit 150, and transmits control signals 104 to motor driver circuit 150 suitable for causing the motor or actuator to generate the output motion that follows the targeted velocity profile. The target trajectory generally includes a fast deceleration profile that satisfies an IEC stopping distance for the actuator or motor associated with motor driver circuit 150. Thus, in Fast Ramp Down state 705, when an operator stops depressing mechanical switch 121 with a conductive object and removes the previously detected conductive object from the capacitive sensing region of capacitive sensor 122, controller 110 stops the output motion of motor driver circuit 150 quickly. That is, motion enable system 100 enters Fast Ramp Down state 705 in response to the operator completely removing the digit or conductive stylus that was previously depressing the mechanical switch of motion enable device 120. In this way, an operator can cause controller 110 to initiate a fast ramp-down of the output motion of motor driver circuit 150 to avoid a collision, rather than a smoother but slower ramp-down of the output motion of motor driver circuit 150.

It is noted that in some embodiments, when motion enable system 100 enters Fast Ramp Down state 705, rather than removing power connection 109 to motor driver circuit 150 so that a motor or actuator coasts to a stop, motor driver circuit 150 is employed to actively decelerate the motor or actuator so that the output motion of motor driver circuit 150 is less than or equal to an IEC stopping distance.

In some embodiments, while motion enable system 100 is in Fast Ramp Down state 705, controller 110 continues the fast ramp-down timer. Upon expiration of the fast ramp-down timer, controller 110 stops sending power enable signal 103 to power enable switch 130, motor control circuit 150 is not longer powered, and motion enable system 100 enters Power Off state 701.

Figure 8:
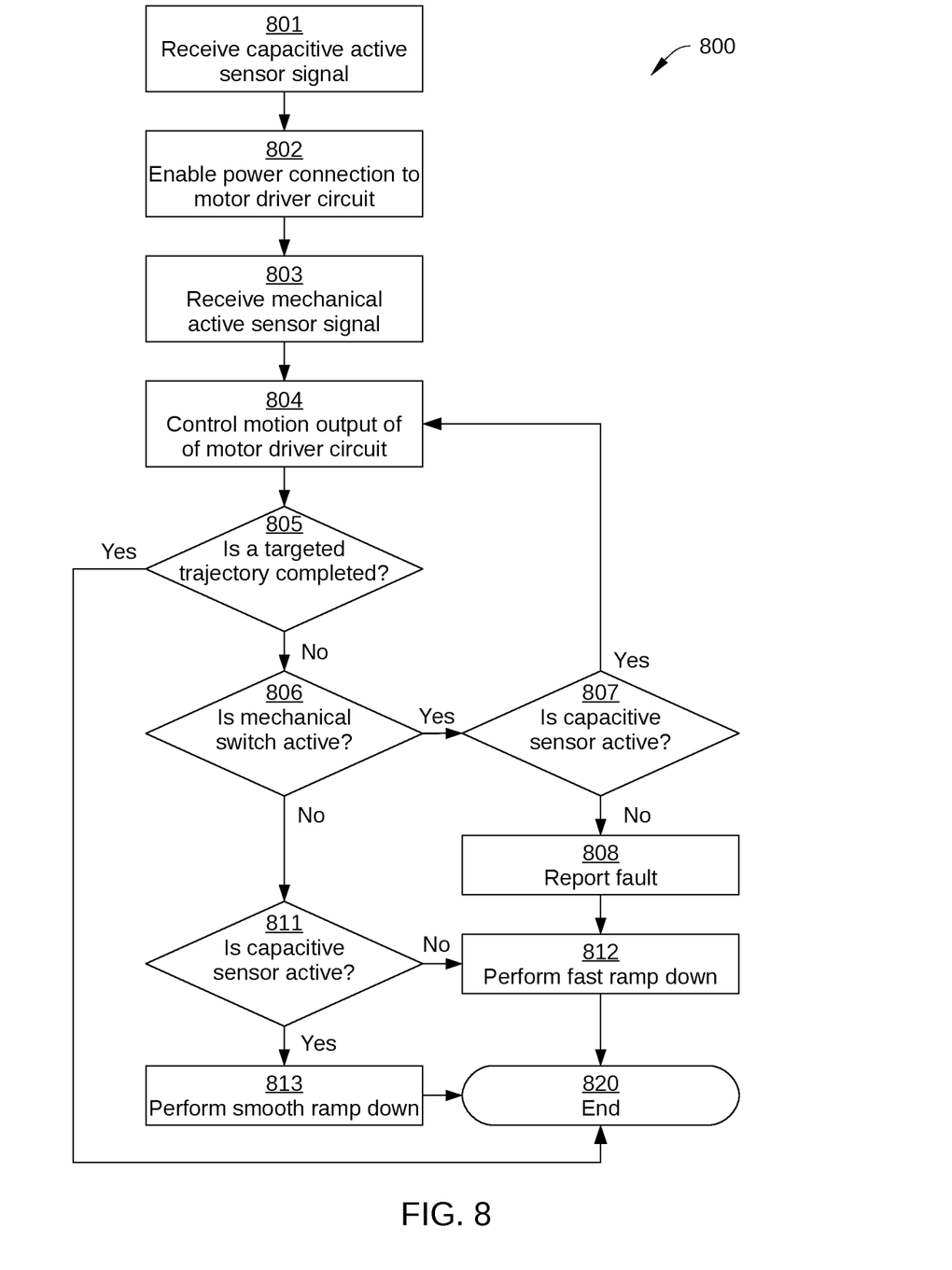
FIG. 8 sets forth a flowchart summarizing an example method for enabling the motion tracking of an actuator, according to one or more embodiments of the present disclosure.

FIG. 8 sets forth a flowchart summarizing an example method for enabling the motion tracking of an actuator, according to one or more embodiments of the present disclosure. The method may include one or more operations, functions, or actions as illustrated by one or more of blocks 801-820. Although the blocks are illustrated in a sequential order, these blocks may be performed in parallel, and/or in a different order than those described herein. Also, the various blocks may be combined into fewer blocks, divided into additional blocks, and/or eliminated based upon the desired implementation. Although the method is described in conjunction with motion enable system 100 of FIG. 1, persons skilled in the art will understand that any suitably configured system is within the scope of the present disclosure. In the embodiment described in conjunction with FIG. 8, the control algorithms for the method steps reside in and/or are performed by controller 110. In other embodiments, such control algorithms may reside in and/or be performed by any other suitable control circuit or computing device.

A method 800 begins at step 801, in which controller 110 receives capacitive sensor active signal 102 from capacitive sensor 122, for example when an operator moves a digit or other conductive object within a sensing region of capacitive sensor 122.

In step 802, controller 110 enables power connection 109 between power source 140 and motor driver circuit 150. For example, in some embodiments, controller 110 transmits power enable signal 103 to power enable switch 130.

In step 803, controller 110 receives mechanical switch active signal 101 while still receiving capacitive sensor active signal 102. For example, controller 110 receives mechanical switch active signal 101 when the operator depresses or actuates mechanical switch 121.

In step 804, in response to receiving mechanical switch active signal 101 while still receiving capacitive sensor active signal 102, controller 110 controls a motion output of motor driver circuit 150 to follow a targeted trajectory or velocity profile, for example via control signal 104. The targeted trajectory or velocity profile can be determined based on various factors, such as which particular mechanical switch 121 has been depressed and for how long that particular mechanical switch 121 has been depressed.

In step 805, controller 110 determines whether the targeted trajectory has been completed, such as when the targeted trajectory is defined by a preprogrammed motion. If yes, method 800 proceeds to step 820 and terminates; if no, method 800 proceeds to step 806. Generally, step 805 is performed while controller 110 controls the motion output of motor driver circuit 150 as described in step 804.

In step 806, controller 110 determines whether mechanical switch 121 is still active. That is, controller 110 determines whether mechanical switch active signal 101 is still being received. If yes, method 800 proceeds to step 807; if no, the operator is no longer depressing or actuating motion enable device 120, and method 800 proceeds to step 811.

In step 807, controller 110 determines whether capacitive sensor 122 is still active. That is, controller 110 determines whether capacitive sensor active signal 102 is still being received. If yes, motion enable device 120 is operating properly and method 800 proceeds back to step 804; if no, motion enable device 120 is not operating properly, since, capacitive sensor 122 should always be active when mechanical switch 121 is active. Thus, when controller 110 determines in step 807 that capacitive sensor 122 is not active, a fault is detected and method 800 proceeds to step 808.

In step 808, controller 110 reports the fault detected in step 807. Method 800 then proceeds to step 812 and a fast ramp down is performed, as shown. Alternatively, after controller 110 reports the detected fault, the motion output of motor driver circuit 150 is stopped in some other suitable fashion, and method 800 proceeds directly to step 820 and terminates.

In step 811, which is performed in response to controller 110 determining that mechanical switch 121 is no longer active, controller 110 determines whether capacitive sensor 122 is still active. That is, controller 110 determines whether capacitive sensor active signal 102 still being received. If yes, then the operator continues to hold a digit or other conductive object proximate motion enable switch 120, and method 800 proceeds to step 813 for a smooth ramp-down to be performed; if no, then the operator has completely removed the digit or conductive object from motion enable device 120, and method 800 proceeds to step 812 for a fast ramp-down to be performed.

In step 812, controller 110 controls the output motion of motor driver circuit 150 so that a fast ramp-down is performed. Typically, the fast ramp-down is performed so that an IEC stopping distance for the actuator or motor associated with motor driver circuit 150 is achieved. Method 800 then proceeds to step 820 and terminates.

In step 813, controller 110 controls the output motion of motor driver circuit 150 so that a smooth ramp-down is performed. Typically, the smooth ramp-down is performed so that the actuator or motor associated with motor driver circuit 150 generates an output motion that follows an S-curve acceleration profile that reduces or eliminates jerk. Method 800 then proceeds to step 820 and terminates.

In sum, embodiments described herein include a motion enablement system that meets IEC standards, including initiating motion of an associated apparatus when two separate switches or control devices have been actuated by the operator. In addition, the herein described motion enablement system is configured to stop motion of the associated apparatus within an IEC stopping distances when the operator ceases actuating both control devices. The motion enable system is further configured to minimize or otherwise reduce the potential for repetitive stress injuries in an operator.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The invention claimed is:
1. A motion-enable system, comprising:
  an actuator;
  a mechanical switch that includes an interface surface that is disposed on a first side of the mechanical switch and configured to receive a physical input, the mechanical switch including a second side that is different from the first side;
  a capacitive sensor with a first sensing region that extends past the interface surface of the mechanical switch and a second sensing region that extends further past the interface surface than the first sensing region, wherein the capacitive sensor is configured to enable a second signal when a conductive object is disposed in the second sensing region and a first signal when the conductive object is disposed in the first sensing region, and wherein the second signal indicates that the capacitive sensor is in a second active state and the first signal indicates that the capacitive sensor is in a first active state, and
  a controller configured to perform the steps of:
  changing the actuator from a first power state to a second power state in response to the capacitive sensor changing from the second active state to the first active state;
  maintaining the actuator in the second power state in response to the capacitive sensor changing from the first active state to the second active state; and
  changing the actuator from the second power state to a third power state, in response to the mechanical switch entering a third active state while the capacitive sensor is in the first active state, wherein
  the mechanical switch is configured to enable a third signal when the mechanical switch is actuated from a first position to a second position by the physical input,
  the third signal indicates that the mechanical switch is in the third active state, and
  each of the first power state, the second power state, and the third power state corresponds to a different power connection state of the motion-enable system.

2. The motion-enable system of claim 1, wherein the first power state comprises a power off state for the actuator.

3. The motion-enable system of claim 2, wherein, in the power off state, there is no power connection between a power source and a motor driver circuit associated with the actuator.

4. The motion-enable system of claim 3, wherein the actuator is included in the motor driver circuit.

5. The motion-enable system of claim 1, wherein the second power state comprises a power on state for the actuator in which there is a power connection between a power source and a motor driver circuit associated with the actuator.

6. The motion-enable system of claim 1, wherein the third power state comprises a motion enable state in which the actuator receives control signals and responds to the control signals.

7. The motion-enable system of claim 6, wherein the control signals cause a targeted motion trajectory of the actuator.

8. A method for a motion-enable system that includes a capacitive sensor, an actuator, and a mechanical switch with an interface surface that is disposed on a first side of the mechanical switch and configured to receive a physical input, the method comprising:
  determining that the capacitive sensor has changed to a first active state in response to a conductive object being disposed in a first sensing region of the capacitive sensor that extends past the interface surface of the mechanical switch;

in response to determining that the capacitive sensor has changed to the first active state, changing the actuator from a first power state to a second power state;

while the actuator is in the second power state, determining that the capacitive sensor has changed from the first active state to a second active state in response to the conductive object not being disposed in the first sensing region and being disposed in a second sensing region of the capacitive sensor, wherein the second sensing region extends further past the interface surface of the mechanical switch than the first sensing region;

in response to determining that the capacitive sensor has changed to the first active state from the second active state, maintaining the actuator in the second power state; and changing the actuator from the second power state to a third power state, in response to the mechanical switch entering a third active state while the capacitive sensor is in the first active state, wherein the mechanical switch is configured to enable a third signal when the mechanical switch is actuated from a first position to a second position by the physical input, the third signal indicates that the mechanical switch is in the third active state, and each of the first power state, the second power state, and the third power state corresponds to a different power connection state of the motion-enable system.

9. The method of claim 8, wherein the capacitive sensor is disposed on a second side of the actuator, wherein the first side is different from the second side.

10. The method of claim 8, wherein determining that the capacitive sensor has changed to the first active state comprises receiving a first signal enabled by the capacitive sensor when the conductive object is disposed in the first sensing region of the capacitive sensor.

11. The method of claim 8, wherein determining that the capacitive sensor has changed to the second active state comprises receiving a second signal enabled by the capacitive sensor when the conductive object is disposed in the second sensing region of the capacitive sensor and not in the first sensing region of the capacitive sensor.

12. The method of claim 8, wherein the first power state comprises a power off state for the actuator.

13. The method of claim 12, wherein, in the power off state, there is no power connection between a power source and a motor driver circuit associated with the actuator.

14. The method of claim 13, wherein the actuator is included in the motor driver circuit.

15. The method of claim 8, wherein the second power state comprises a power on state for the actuator in which there is a power connection between a power source and a motor driver circuit associated with the actuator.

16. The method of claim 8, wherein the third power state comprises a motion enable state in which the actuator receives control signals and responds to the control signals.

* * * * *